(12) United States Patent
Kanauchi (10) Patent No.: US 10,918,766 B2
(45) Date of Patent: Feb. 16, 2021

(54) AGENT FOR HYPODERMIC INJECTION (71) Applicant: Motejo Ltd., Tokyo (JP)

(72) Inventor: Atsushi Kanauchi, Tokyo (JP)

(73) Assignee: Motejo Ltd., Tokyo (JP)

( * ) Notice: Subject to any disclaimer, the term of this patent is extended or adjusted under 35 U.S.C. 154(b) by 0 days.

(21) Appl. No.: 15/535,358

(22) PCT Filed: Sep. 14, 2015

(86) PCT No.: PCT/JP2015/076068
§ 371 (c)(1),
(2) Date: Jun. 12, 2017

(87) PCT Pub. No.: WO2016/092928
PCT Pub. Date: Jun. 16, 2016

(65) Prior Publication Data
US 2017/0333600 A1    Nov. 23, 2017

(30) Foreign Application Priority Data

Dec. 12, 2014 (JP) ................................ 2014-252327
Jun. 26, 2015 (JP) ................................ 2015-129289

(51) Int. Cl.
| | | |
|---|---|---|
| A61L 27/50 | (2006.01) | |
| A61L 27/00 | (2006.01) | |
| A61K 47/38 | (2006.01) | |
| A61K 33/42 | (2006.01) | |
| A61K 9/08 | (2006.01) | |
| A61L 27/12 | (2006.01) | |
| A61L 27/20 | (2006.01) | |
| A61L 27/52 | (2006.01) | |

(52) U.S. Cl.
CPC ............... *A61L 27/50* (2013.01); *A61K 9/08* (2013.01); *A61K 33/42* (2013.01); *A61K 47/38* (2013.01); *A61L 27/00* (2013.01); *A61L 27/12* (2013.01); *A61L 27/20* (2013.01); *A61L 27/52* (2013.01); *A61L 2400/06* (2013.01); *A61L 2430/34* (2013.01)

(58) Field of Classification Search
None
See application file for complete search history.

(56) References Cited

U.S. PATENT DOCUMENTS

| | | |
|---|---|---|
| 5,344,644 A | 9/1994 | Igari et al. |
| 5,717,006 A | 2/1998 | Daculsi et al. |
| 7,060,287 B1 | 6/2006 | Hubbard et al. |
| 2002/0151466 A1 | 10/2002 | Hubbard et al. |
| 2004/0185021 A1 | 9/2004 | Hubbard |
| 2006/0173551 A1 | 8/2006 | Hubbard et al. |
| 2007/0259047 A1 | 11/2007 | Ogawa et al. |
| 2008/0226722 A1 | 9/2008 | Van Tomme et al. |
| 2010/0100179 A1 | 4/2010 | Hubbard |
| 2010/0240946 A1 | 9/2010 | Hubbard et al. |
| 2011/0125288 A1 | 5/2011 | Hubbard et al. |
| 2011/0280864 A1 | 11/2011 | Johnston et al. |
| 2011/0280932 A1 | 11/2011 | Garcia et al. |
| 2012/0128788 A1 | 5/2012 | Kogai et al. |
| 2013/0060230 A1* | 3/2013 | Capistron ............... A61K 8/24 604/506 |
| 2013/0183370 A1 | 7/2013 | Garcia et al. |
| 2013/0183371 A1 | 7/2013 | Garcia et al. |
| 2014/0378370 A1 | 12/2014 | Johnston et al. |
| 2015/0064260 A1 | 3/2015 | Kogai et al. |

FOREIGN PATENT DOCUMENTS

| | | |
|---|---|---|
| CN | 102458423 A | 5/2012 |
| EP | 1719523 A1 | 11/2006 |
| JP | H05-186364 A | 7/1993 |
| JP | 2003-507351 A | 2/2003 |
| JP | 3559565 B2 | 9/2004 |
| JP | 2007-1865 A | 1/2007 |
| JP | 2007-537249 A | 12/2007 |
| JP | 2012-508744 A | 4/2012 |
| JP | 2013-526545 A | 6/2013 |
| JP | 5774189 B1 | 9/2015 |
| JP | 5797864 B1 | 10/2015 |
| WO | 01/12247 A1 | 2/2001 |
| WO | 2005/025542 A1 | 3/2005 |
| WO | 2005/082405 A1 | 9/2005 |
| WO | 2010/137122 A1 | 12/2010 |

OTHER PUBLICATIONS

International Preliminary Report on Patentability issued in corresponding International Application No. PCT/JP2015/076068; dated Jun. 22, 2017 (11 pages).

International Search Report issued in PCT/JP2015/076068 dated Dec. 8, 2015 (7 pages).

Written Opinion of the International Searching Authority issued in PCT/JP2015/076068 dated Dec. 8, 2015 (6 pages).

Thioly-Bensoussan, D. et al.; "Non-hyaluronic acid fillers"; Elsevier, Clinics in Dermatology, vol. 26, No. 2, 2008, pp. 160-176, pp. 164 to 165, 'Radiesse', paragraphs of 'Context', 'Structure', 'Mechanism of action', 'Technique' (17 pages).

(Continued)

*Primary Examiner* — James W Rogers
(74) *Attorney, Agent, or Firm* — Osha Bergman Watanabe & Burton LLP (57) ABSTRACT

To provide an agent for hypodermic injection that has excellent flow characteristics, can be used particularly even in thin injection needles, for example with an internal diameter of 0.20 mm or less, and is unlikely to cause pain during injection and inflammation.

The agent for hypodermic injection includes a hydrogel containing sintered hydroxyapatite particles, wherein the sintered hydroxyapatite particle content is 1 to 60% by mass based on the total mass of the agent, and the average particle diameter of the sintered hydroxyapatite particles is 15 μm or less.

10 Claims, 2 Drawing Sheets

(56) References Cited

OTHER PUBLICATIONS

Ji et al.; "A novel injectable chitosan/ployglutamate polyelectrolyte complex hydrogel with hydroxyapatite for soft-tissue augmentation"; Carbohydrate Polymers, vol. 89, No. 4, 2012, pp. 1123-1230, p. 1123, right column, lines 6 to 8 (8 pages).
Office Action issued in Taiwanese Application No. 105119917; dated Jul. 17, 2017 (12 pages).
Extended European Search Report issued in European Application No. 15867438.2, dated Jul. 9, 2018 (6 pages).
Office Action issued in corresponding Chinese Application No. 201580067195.4; dated Dec. 13, 2019 (8 pages).

* cited by examiner

AGENT FOR HYPODERMIC INJECTION

CROSS-REFERENCE TO RELATED APPLICATIONS

This application is a national stage of International Application No. PCT/JP2015/076068 with a filing date of 14 Sep. 2015, which claims priority to Japanese Patent Application No. 2015-129289 with a filing date of 26 Jun. 2015 and Japanese Patent Application No. 2014-252327 with a filing date of 12 Dec. 2014, the contents of which are incorporated herein by reference.

TECHNICAL FIELD

The present invention relates to an agent for hypodermic injection.

BACKGROUND ART

In the cosmetic medical field, a filling material (filler) containing hydroxyapatite is injected under the skin as a means for improving beauty. Hydroxyapatite has various effects including biocompatibility, and is a material which is expected to have an excellent effect for improving beauty even by hypodermic injection.

Patent Literature 1, for example, discloses a biomaterial composition which uses particles containing calcium hydroxyapatite with a particle diameter of 80 to 200 μm.

CITATION LIST

Patent Literature

Patent Literature 1: JP 3559565 B2

SUMMARY OF INVENTION

Technical Problem

The composition described in Patent Literature 1 above, however, has not necessarily had good flow characteristics. As a result, it has been required to select a needle with a large needle diameter (an internal diameter of 0.21 mm or more) as an injection needle, which has caused problems in that, for example, pain occurs during injection.

In the case of the particle diameter of calcium hydroxyapatite particles described in Patent Literature above, there have been problems in that, for example, the particles are recognized as a foreign substance by macrophages to cause inflammation.

Therefore, a subject of the present invention is to provide an agent for hypodermic injection that has excellent flow characteristics, can be used particularly even in thin needles, for example with an internal diameter of 0.20 mm or less, and is unlikely to cause pain during injection and inflammation.

Solution to Problem

The inventors diligently repeated investigations to solve the above problems. As a result, the inventors found that by producing an agent containing specific hydroxyapatite particles in a specific amount, the flow characteristics of the agent could be significantly improved, thereby completing the present invention. That is, the present invention is as follows.

The present invention (1) is
an agent for hypodermic injection including
a hydrogel containing sintered hydroxyapatite particles, wherein
a content of the sintered hydroxyapatite particle is 1 to 60% by mass based on the total mass of the agent, and
an average particle diameter of the sintered hydroxyapatite particles is 15 μm or less.
The present invention (2) is
the agent according to the invention (1), wherein 90% or more of the sintered hydroxyapatite particles have a particle diameter of 15 μm or less.
The present invention (3) is
the agent according to the invention (1) or (2), wherein 4% or more of the sintered hydroxyapatite particles have a particle diameter of 5 μm or more and 30 μm or less.
The present invention (4) is
the agent according to any of the inventions (1) to (3), wherein the sintered hydroxyapatite particles are for promoting collagen production.
The present invention (5) is
the agent according to any of the inventions (1) to (4), wherein the hydrogel is a carboxymethylcellulose gel.
The present invention (6) is
the agent according to any of the inventions (1) to (5), wherein the viscosity of the hydrogel is 50 to 15000 mPa·s.
The present invention (7) is
the agent according to any of the inventions (1) to (6), wherein the agent passes through a hollow needle with an internal diameter of 0.20 mm or less.
The present invention (8) is
a method for producing an agent for hypodermic injection, the method including
the step of mixing sintered hydroxyapatite particles and a hydrogel, wherein
a content of the sintered hydroxyapatite particle is 1 to 60% by mass based on the total mass of the agent, and
an average particle diameter of sintered hydroxyapatite particles in the agent is 15 μm or less.
The present invention (9) is
the production method according to the invention (8), wherein 90% or more of sintered hydroxyapatite particles in the agent have a particle diameter of 15 μm or less.
The present invention (10) is
the production method according to the invention (8) or (9), wherein 4% or more of sintered hydroxyapatite particles in the agent have a particle diameter of 5 μm or more and 30 μm or less.
The present invention (11) is
the production method according to any of the inventions (8) to (10), wherein the sintered hydroxyapatite particles are for promoting collagen production.
The present invention (12) is
the production method according to any of the inventions (8) to (11), wherein the hydrogel is a carboxymethylcellulose gel.
The present invention (13) is
the production method according to any of the inventions (8) to (12), wherein the viscosity of the hydrogel is 50 to 15000 mPa·s.
The present invention (14) is
the production method according to any of the inventions (8) to (13), wherein the agent passes through a hollow needle with an internal diameter of 0.20 mm or less.

Advantageous Effects of Invention

According to the present invention, it is possible to provide an agent for hypodermic injection that has excellent flow characteristics, can be used particularly even in thin needles, for example with an internal diameter of 0.20 mm or less, and is unlikely to cause pain during injection and inflammation.

DESCRIPTION OF EMBODIMENTS

An agent for hypodermic injection according to a preferred embodiment of the present invention will be described in the following order:
(1) the composition of the agent for hypodermic injection,
(2) a method for producing the agent for hypodermic injection,
(3) the action of the agent for hypodermic injection,
(4) a method for using the agent for hypodermic injection, and
(5) the physical properties of the agent for hypodermic injection.
<<Composition>>

The components of the agent for hypodermic injection according to the present embodiment and the amounts blended will now be described in detail.
<Components>

The agent for hypodermic injection according to the present embodiment includes hydroxyapatite particles and a hydrogel and furthermore may include other components. It should be noted that hydroxyapatite particle aggregates are aggregates of hydroxyapatite particles.
(Hydroxyapatite Particles)

First, the hydroxyapatite (calcium phosphate hydroxide) particles according to the present embodiment will be described about their composition, functions and characteristics, acquisition method, sintering, and particle diameter. It should be noted that the physical properties (particularly, the particle diameter) of hydroxyapatite particles described herein indicate the physical properties of hydroxyapatite particles contained in an agent for hypodermic injection (the physical properties of hydroxyapatite particles contained in the agent for hypodermic injection and the physical properties of hydroxyapatite particles, a constituent of the agent for hypodermic injection, are not necessarily identical because, for example, their forms can be changed in the production stage.)
Composition Hydroxyapatite (HAp) is basic calcium phosphate represented by the chemical formula $Ca_{10}(PO_4)_6(OH)_2$, and exists as the main component of teeth and bones and also occurs naturally as an ore.
Functions and Characteristics Hydroxyapatite particles show high biocompatibility. In particular, when using them as an agent for hypodermic injection, hydroxyapatite particles existing as nanoparticles in a filler stimulate fibroblasts to promote collagen production. In addition, hydroxyapatite particles existing as microparticles in a filler physically function as a spacer.
Sintering As the hydroxyapatite particles according to the present embodiment, sintered hydroxyapatite particles (hereinafter, "hydroxyapatite particles" mean "sintered hydroxyapatite particles" unless otherwise specified) are used. By sintering hydroxyapatite particles (e.g. at 800° C. for an hour), the crystallinity of particles increases, and a plurality of aggregates of primary particles are fused due to heat to obtain more solid and stable particles. In particular, sintering by a dispersion-sintering method is appropriate, and apatite nanoparticles which are not easily aggregated and have high crystallinity can be obtained by sintering using a fusion preventing agent. As described above, the concept of "hydroxyapatite particles" described in the present invention includes not only sintered hydroxyapatite particles with a primary particle size but also aggregates in which a plurality of primary particles are fused unless otherwise specified.

Using such sintered apatite particles, a filler having a high effect for stimulating fibroblasts to promote collagen production can be obtained. That is, by changing hydroxyapatite particles into sintered hydroxyapatite, the action of promoting collagen production is significantly improved compared to that of unsintered hydroxyapatite. Furthermore, sintered hydroxyapatite has high crystallinity and low solubility in the body compared to those of amorphous hydroxyapatite. Therefore, bioactivity can be maintained in the body for a long period of time, and thus the effect of promoting collagen production is easily shown for a long period of time.

Sintered hydroxyapatite particles are obtained by sintering amorphous hydroxyapatite. More particularly, sintered hydroxyapatite can be obtained, for example, by sintering amorphous hydroxyapatite in a dispersion-sintering method. In addition, hydroxyapatite particles with high crystallinity, high-crystalline hydroxyapatite particles, are appropriately used.

The lower limit of sintering temperature is more preferably 500° C. or higher. When the sintering temperature is lower than 500° C., sintering is insufficient in some cases. On the other hand, the upper limit of sintering temperature is more preferably 1800° C. or lower, further preferably 1250° C. or lower, and particularly preferably 1200° C. or lower. When the sintering temperature is higher than 1800° C., hydroxyapatite can be decomposed. Therefore, hydroxyapatite which is not easily dissolved in the body (high crystallinity) can be produced by adjusting the sintering temperature to the above range. In addition, sintering time is not particularly limited, and can be suitably set. It should be noted that particles can be fused by sintering, and in this case, particles after sintering can be pulverized and used.

It can be determined whether hydroxyapatite particles are sintered or not by the degree of crystallinity of such particles. The degree of crystallinity of hydroxyapatite particles can be measured by an X-ray diffraction method (XRD). It can be said that as the half width of each crystal plane peak is narrower, crystallinity is higher. More particularly, the sintered hydroxyapatite particles in the present embodiment are high crystalline hydroxyapatite particles in which the half width of the peak of the (300) plane around $2\theta=32°$ in X-ray diffraction (CuK α line) is appropriately 0.8 or less (more appropriately 0.5 or less).

As described above, apatite nanoparticles which are not easily aggregated and have high crystallinity can be obtained by sintering using a fusion preventing agent. The fusion preventing agent is not particularly limited as long as fusion between hydroxyapatite particles can be prevented, and the fusion preventing agent is preferably nonvolatile at the above sintering temperature. However, it is only required that the fusion preventing agent be nonvolatile to the extent that 10% or more of the fusion preventing agent remains after completion of the sintering step. The fusion preventing agent can be also one which is chemically decomposed by heat after completion of the sintering step. Furthermore, the fusion preventing agent is preferably a substance which is dissolved in a solvent, particularly a water-based solvent. This is because the fusion preventing agent can be removed only by suspending hydroxyapatite particles mixed together with the fusion preventing agent in a water-based solvent.

Specific examples of such fusion preventing agents include calcium salts (or complexes) such as calcium chloride, calcium oxide, calcium sulfate, calcium nitrate, calcium carbonate, calcium hydroxide, calcium acetate and calcium citrate, potassium salts such as potassium chloride, potassium oxide, potassium sulfate, potassium nitrate, potassium carbonate, potassium hydroxide and potassium phosphate, sodium salts such as sodium chloride, sodium oxide, sodium sulfate, sodium nitrate, sodium carbonate, sodium hydroxide and sodium phosphate, and the like.

Acquisition Method

A general method for producing hydroxyapatite particles is for example a solution method (wet process). This is a method in which a calcium ion and a phosphate ion are allowed to react in a neutral or alkaline aqueous solution to synthesis hydroxyapatite particles, and there are a method by neutralization and a method in which a calcium salt and a phosphoric salt are allowed to react. As described above, crystalline apatite particles with a little aggregation are obtained by sintering in the coexistence of a fusion preventing agent.

Particle Diameter

The particle diameter (average particle diameter) of hydroxyapatite particles according to the present embodiment is 15 μm or less, appropriately 5 μm or less, more appropriately 1 μm or less and further appropriately 100 nm or less. By adjusting the particle diameter to such range, fibroblasts are stimulated to promote collagen production. By adjusting the particle diameter to such range, because of the size which is not easily recognized as a foreign substance in the body, macrophages are not easily induced. The lower limit of particle diameter (average particle diameter) of hydroxyapatite particles is not particularly limited, and for example, 10 nm or more. It should be noted that the average particle diameter of hydroxyapatite particles (including aggregates) in a filler described herein is determined from an average diameter obtained by measuring the particle diameter of particles (e.g. 50 particles) in an image taken by a microscope. The average particle diameter can be also determined from an average diameter obtained by swelling a filler with e.g. water, dissolving a hydrogel therein and measuring the particle diameter of particles (e.g. 50 particles) of hydroxyapatite taken therefrom. The average particle diameter of hydroxyapatite particles (including aggregates) in a filler described herein can be also determined by measuring the particle size distribution using a high-concentration measurement unit of a laser diffraction particle size analyzer (SALD-7500 manufactured by SHIMADZU CORPORATION) and obtaining 50% volume particle diameter (D50) from the measurement results of particle size distribution. More particularly, a filler is put between slide glasses (S7213 MATSUNAMI GLASS IND., LTD.) with the filler drawn as much as possible and the particle size distribution is measured with a refractive index of 1.65.

With respect to the particle diameter of hydroxyapatite particles in the agent according to the present embodiment, it is only required that the particle diameter of almost all particles be in a desired range as a practical issue, and the particle diameter of some particles can be outside the desired range without inhibiting the effect of the invention. More particularly, 90% or more of particles are preferably in a desired range (15 μm or less, appropriately 10 μm or less, more appropriately 5 μm or less, and particularly appropriately 1 μm or less), more preferably 95% or more of particles are in the desired range, further preferably 97% or more of particles are in the desired range, and particularly preferably 99% or more of particles are in the desired range. An agent thus produced can be stably used even in thin needles, for example with an internal diameter of 0.20 mm or less. The range of particles described herein is based on the measurement results of particle diameter of particles (e.g. 100 particles) in an image taken by a microscope and can be also based on the particle size distribution obtained by a laser diffraction particle size analyzer described below. As described below, when considering the reaggregation properties of particles in an agent for hypodermic injection, a preferred distribution about the particle diameter of particles can be provided from different viewpoints.

Herein, when hydroxyapatite particles have a nano order particle diameter, the viscosity of an agent for hypodermic injection can increase. Such increase in viscosity is advantageous in the respect that an agent for hypodermic injection remains under the skin; however, when the viscosity increases too much, injection from an injection needle can be difficult. From such viewpoint, the particle diameter of hydroxyapatite particles is appropriately 15 nm or more, more appropriately 20 nm or more, and particularly appropriately 100 nm or more.

As described above, hydroxyapatite particles in the agent for hypodermic injection according to the present embodiment function, for example, as a component having the action of promoting collagen production and a component which improves viscosity, and furthermore can be a component which induces macrophages. The particle diameter of hydroxyapatite particles is appropriately 10 nm to 8 μm in the respect that all of these functions are made suitable.

Herein, in an agent for hypodermic injection containing sintered hydroxyapatite particles, there has been a problem in that the reaggregation of hydroxyapatite particles occurs at the time of heat sterilization. When reaggregation occurs, the flow characteristics of an agent for hypodermic injection can be reduced.

As a result of repeated diligent investigations to solve the above problem, the present inventors found that, by producing an agent for hypodermic injection containing specific hydroxyapatite particles in a specific amount, the flow characteristics of the agent for hypodermic injection could be significantly improved, and the reaggregation of hydroxyapatite was unlikely to occur at the time of heat sterilization. The constitution of sintered hydroxyapatite particles in an agent for hypodermic injection, in which the reaggregation of hydroxyapatite can be prevented, will now be described in detail.

As described above, crystalline apatite particles with a little aggregation can be obtained by sintering in the coexistence of a fusion preventing agent; however, when apatite particles with a large particle diameter do not exist at a fixed proportion in the particle size distribution of apatite particles, the reaggregation of apatite particles easily occurs at the time of heat sterilization. It is thought that this is because the viscosity of a filler is reduced at the time of heat sterilization to liquefy the filler and thus fine apatite particles are reaggregated due to Brownian motion.

When the reaggregation of apatite particles occurs, the flow characteristics of an agent for hypodermic injection is reduced. In other words, a gel and apatite particles are separated, and apatite particles are aggregated, and thus there is a risk that force required to pass through 30 G needles increases.

Therefore, it is appropriate that 4% or more of apatite particles have a particle diameter of 5 μm or more and 30 μm or less, and it is more appropriate that 5% or more of apatite particles have a particle diameter of 5 μm or more and 30 μm or less. In addition, it is appropriate that 3% or more of apatite particles have a particle diameter of 6 μm or more and 30 μm or less, and it is more appropriate that 4% or more of apatite particles have a particle diameter of 6 μm or more and 30 μm or less. By adjusting the particle diameter to such range, in the agent for hypodermic injection of the present invention that has excellent flow characteristics, can be used particularly even in thin needles, for example with an internal diameter of 0.20 mm or less, and is unlikely to cause pain and inflammation during injection, furthermore, it is possible that the reaggregation of hydroxyapatite particles is not made to easily occur.

When focusing also on the reaggregation of hydroxyapatite particles as described above, the particle diameter (average particle diameter) of hydroxyapatite particles is 15 μm or less, appropriately 10 μm or less, more appropriately 5 μm or less, still more appropriately 3 μm or less, and further appropriately 1 μm or less.

The upper limit of proportion of apatite particles with a large particle diameter can be determined from a relationship with the average particle diameter described above.

The particle size distribution can be measured using a high-concentration measurement unit of a laser diffraction particle size analyzer (SALD-7500 manufactured by SHIMADZU CORPORATION) as described above. More particularly, a filler is put between slide glasses (S7213 MATSUNAMI GLASS IND., LTD.) with the filler drawn as much as possible and the particle size distribution is measured with a refractive index of 1.65.

(Hydrogel)

The hydrogel is not particularly limited as long as it can be used for an agent for hypodermic injection, and examples thereof include carboxymethylcellulose gels (CMC), polyvinyl alcohol gels, sodium polyacrylate gels [e.g. Carbopol (registered trademark) etc.] A carboxymethylcellulose gel is preferred, for example, because cellulose, a material, is safe and cheap.

Carboxymethylcellulose Gel

Carboxymethylcellulose (CMC) is a cellulose ether in which a carboxymethyl group is introduced into a hydroxy group of cellulose. In the present embodiment, CMC is not particularly limited and is preferably sodium carboxymethylcellulose (Na-CMC) which is a sodium salt of CMC.

The degree of etherification of commercially available CMC is about 0.5 to 1.0. In addition, CMC with a degree of etherification of 3, in which all the three hydroxy groups per cellulose unit are etherified, can be produced, and CMC with a degree of etherification of 1.0 or more is also commercially available. The degree of etherification of CMC can be obtained by a mineral alkaline method published by CMC Kogyokai. In the present embodiment, the degree of etherification is preferably 0.5 or more, more preferably 0.8 or more, and further preferably 1.0 or more. It should be noted that the degree of etherification generally indicates the average number of hydroxy groups substituted with a carboxymethyl group or a salt thereof among hydroxy groups in a glucose residue forming cellulose.

The molecular weight of CMC is preferably 50,000 to 500,000. When this molecular weight is less than 50,000, viscosity becomes low and thixotropic properties deteriorate. On the other hand, when the molecular weight is above 500,000, viscosity becomes too high, and the amount of injectable apatite blended becomes insufficient. It should be noted that the molecular weight described herein indicates weight average molecular weight and can be measured by gel permeation chromatography.

The method for producing a carboxymethylcellulose gel is not particularly limited, and for example a carboxymethylcellulose gel can be produced by blending carboxymethylcellulose, glycerin and water. The weight ratio of components blended is not particularly limited, and is preferably carboxymethylcellulose:glycerin:water=1:5 to 20:30 to 60, and further preferably 1:7 to 15:40 to 55 due to an appropriate range of viscosity as described below.

A carboxymethylcellulose (CMC) gel is a physical gel having thixotropic properties, and behaves as an elastic body when a shear stress is zero or near zero, and shows a behavior as a fluid as a shear rate increases. This indicates that an agent for hypodermic injection can be easily injected as a fluid with a small force when injected from a needle of a syringe. That is, it can be said that a treatment is easy and the load of patients by the treatment is very light. However, after injected under the skin, the agent for hypodermic injection maintains a shape as an elastic body, and thus remains at a specific site under the skin and has the effect of smoothing wrinkles.

The viscosity of a hydrogel is preferably 50 to 15000 mPa·s, more preferably 55 to 10000 mPa·s, still more preferably 60 to 1000 mPa·s, further preferably 65 to 500 mPa·s, and particularly preferably 70 to 300 mPa·s. When the viscosity of a hydrogel is low, an agent for hypodermic injection cannot maintain a shape after injected under the skin and does not remain at a specific site under the skin. When the viscosity of a hydrogel is high, it is difficult to disperse a sufficient amount of hydroxyapatite particles (hydroxyapatite particles with a small diameter according to the present embodiment) and an agent for hypodermic injection cannot pass through a hollow needle with an internal diameter of 0.20 mm or less. The viscosity can be measured using, for example, a vibration type viscometer in accordance with JIS Z 8803, and more particularly is a value measured by Viscomate MODEL VM-10A.

Hydroxyapatite particles in the range of particle diameter according to the present embodiment have a stronger interaction with a gel skeleton than that of particles beyond the range of particle diameter according to the present embodiment, and thus have the action of suppressing the dissolution of a filler under the skin.

(Other Components)

As other components, known additives such as viscosity modifiers (e.g. glycerin etc.) and dispersing agents (e.g. polyacrylic acid etc.) can be suitably added without inhibiting the effect of the present embodiment.

<Amount to be Blended>

In the agent for hypodermic injection according to the present embodiment, the hydroxyapatite particle content is 1% by mass or more, appropriately 15% by mass or more, more appropriately 20% by mass or more, and further appropriately 30% by mass or more based on the total mass of agent for hypodermic injection. By adjusting the hydroxyapatite particle content to such range, high elasticity is shown and furthermore separation due to precipitation of apatite particles blended in a filler can be prevented. When the hydroxyapatite particle content is less than 1% by mass (particularly less than 15% by mass), the separation between apatite particles and a gel due to storage for a long period of time can be apparent.

The upper limit of the hydroxyapatite particle content is not particularly limited, and is 60% by mass or less, appropriately 50% by mass or less, appropriately 45% by mass or less, and particularly appropriately 40% by mass or less based on the total mass of agent for hypodermic injection. When the hydroxyapatite particle content is above this upper limit, injection from a fine needle with an internal diameter of 0.20 mm or less (furthermore, an internal diameter of 0.18 or less) is difficult, and thus the load of patients at the time of a treatment becomes greater.

Herein, as described above, when hydroxyapatite particles with a small particle diameter are used in the agent for hypodermic injection according to the present embodiment, the viscosity of the agent for hypodermic injection can be higher. However, for example, even when using hydroxyapatite particles with a particle diameter of 100 nm or less (the lower limit is not particularly limited, and for example 20 nm), which have particularly excellent action for promoting collagen production and action in which macrophages are not induced, it is easy to make the viscosity of an agent for hypodermic injection optimum by adjusting the amount of hydroxyapatite particles blended to 40% by mass or less (more appropriately 35% by mass or less) (consequently, the agent for hypodermic injection can be used even in thinner injection needles).

In addition, the hydrogel (particularly a carboxymethylcellulose gel) content is not particularly limited, and is appropriately 0.5% by mass to 2.0% by mass, more appropriately 0.6% by mass to 1.5% by mass, and further appropriately 0.7% by mass to 1.0% by mass in terms of solid matter based on the total mass of agent for hypodermic injection.

It should be noted that the other component content is not particularly limited, and is appropriately 5.0% by mass to 10% by mass, more appropriately 6.0% by mass to 9.0% by mass, and further appropriately 6.5% by mass to 8.8% by mass based on the total mass of agent for hypodermic injection.

<<Production Method>>

Next, a method for producing the agent for hypodermic injection according to the present embodiment will be described.

The agent for hypodermic injection according to the present embodiment can be also adjusted by suitably blending and mixing (stirring) the above materials, and the production method is not particularly limited.

<<Action>>

After subcutaneous injection of the agent for hypodermic injection according to the present embodiment, first, a hydrogel is absorbed and decomposed. The sintered hydroxyapatite particles according to the present embodiment have a small particle diameter and thus the sintered hydroxyapatite particles are released. Fibroblasts are stimulated by the sintered hydroxyapatite particles to promote collagen production. As described above, because of the size which is not easily recognized as a foreign substance in the body, macrophages are not easily induced, and because of high crystallinity, bioactivity can be maintained in the body for a long period of time. As a result, a collagen-rich tissue remains under the skin.

On the other hand, when the average particle diameter of hydroxyapatite particles is larger than that of the present embodiment, apatite acts passively. As the mechanism, because the surface of apatite particles is gradually covered with collagen under the skin due to biocompatibility and furthermore apatite particles have a size which is recognized as a foreign substance, apatite is phagocytized by macrophages, and the collagen layer covering the surface remains, and thus the effect of smoothing wrinkles is sustained.

<<Method of Use>>

The method for using the agent for hypodermic injection according to the present embodiment is not particularly limited, and the agent for hypodermic injection is filled in a syringe of a general injector, and then can be used for subcutaneous injection. In particular, the agent for hypodermic injection can be used as an injectable for a syringe having a hollow needle with an internal diameter of 0.20 mm or less. Herein, as specific methods for using the agent for hypodermic injection according to the present embodiment, an appropriate method for producing a syringe containing the agent for hypodermic injection according to the present embodiment, and a method for applying the agent for hypodermic injection according to the present embodiment will be described. It should be noted that these are just examples and the method for using the agent for hypodermic injection according to the present embodiment is not particularly limited thereto.

<Method for Producing Syringe>

The method for producing the syringe containing an agent for hypodermic injection according to the present embodiment is a method including the deaeration step. Each step will now be described.

(Deaeration Step)

For the agent for hypodermic injection according to the present embodiment, first, air contained in an agent for hypodermic injection is removed by the deaeration step. Due to the characteristics of the agent for hypodermic injection according to the present embodiment, a method by a centrifuge is appropriate as the deaeration step of the agent for hypodermic injection, and a method by a centrifuge under reduced pressure is most appropriate. More particularly, when using a filler having thixotropic properties, for example, having a carboxymethylcellulose (CMC) gel as a main component, the viscosity of the filler can be reduced by adding a shearing force to the filler by centrifugation and the efficiency of deaeration can be raised. Furthermore, by centrifugation under reduced pressure along with the principle of such deaeration, the efficiency of deaeration can be further raised.

The conditions of deaeration are not particularly limited, and include for example the following recipe examples.

Recipe 01 High Viscosity Standard Deaeration
  1.3 KPa 9/3 90 sec (Pressure Revolution/Rotation ratio Time)
Recipe 02 Metal Filler Deaeration
  1.3 KPa 3/9 120 sec
  1.3 KPa 7/5 90 sec
  1.3 KPa 9/2 60 sec
Recipe 03 Ceramic Filler Deaeration
  1.3 KPa 2/5 60 sec
  1.3 KPa 5/5 60 sec By including such deaeration step, air contained in an agent for hypodermic injection having a hydrogel containing sintered hydroxyapatite particles can be removed, and thus inflammation during subcutaneous injection can be suppressed.

(Filling Step)

Next, the agent for hypodermic injection after the deaeration step is filled in a syringe to obtain a syringe according to the present embodiment.

(Disinfection Step)

Furthermore, the agent for hypodermic injection according to the present embodiment can be disinfected and sterilized as needed. A method for disinfection and sterilization is for example high pressure steam sterilization.

<Application Method>

The methods for applying the agent for hypodermic injection and the injector containing an agent for hypodermic injection according to the present embodiment are same as of, for example, conventional agent for hypodermic injections and injectors containing an agent for hypodermic injection and are not particularly limited.

<<Physical Properties>>

The agent for hypodermic injection according to the present embodiment can be used even in thin needles, for example with an internal diameter of 0.20 mm or less, by using a carboxymethylcellulose gel as a main component and sintered hydroxyapatite particles with an average particle diameter of 15 μm or less, even when blending 1 to 60% by mass or more of sintered hydroxyapatite particles based on the total mass of the agent for hypodermic injection. Needles with an internal diameter of 0.20 mm correspond to an injection needle 30 G with a large internal diameter. The agent for hypodermic injection according to the present embodiment can be used in injection needles equal to or thinner than an injection needle 32 G with a large internal diameter (internal diameter 0.18 mm) and in injection needles equal to or thinner than a normal injection needle 30 G (internal diameter 0.14 mm), and can be also used in injection needles equal to or thinner than a normal injection needle 32 G (internal diameter 0.12 mm).

<Thixotropic Properties>

In order to further enhance the effect of the invention, the agent for hypodermic injection according to the present embodiment has appropriately a thixotropic index at 36 to 37° C. (body temperature) of 0.1 to 0.5 and more appropriately 0.1 to 0.3. The thixotropic index is a value measured in the injection characteristics described below.

<Injection Characteristics>

A method for evaluating the injection characteristics of a filler filled in a syringe from a needle will be described. A flow tester according to the present embodiment is used for the method for evaluating injection characteristics. The injection characteristics can be easily evaluated by this flow tester.

More particularly, the flow tester is a flow tester for viscous liquid to evaluate injection characteristics when a viscous liquid filled in an injection cylinder is injected from an injection needle connected to the injection cylinder, the flow tester for viscous liquid including a load applying means for applying a fixed load to the plunger of the injection cylinder in which the viscous liquid is filled, a measuring means for measuring the time dependency of the load when the viscous liquid is injected from the injection needle by the load applying means, and obtaining a flow curve when the viscous liquid is injected from the injection needle from the measurement results by the measuring means. The details of this flow tester will now be described.

First, a 30 G needle with an internal diameter of 0.159 mm and a length of 0.5 inches, for example, is attached to a syringe, and the syringe is then fixed, and a load of 3 kg for example is instantaneously applied to the plunger part. This means for applying a load, i.e. a load applying means for applying a fixed load to the plunger of an injection cylinder in which a viscous liquid is filled is not particularly limited, and for example, a syringe pump is used.

At this time, the filler is discharged from the needle, and the load applied to the plunger decreases over time with the discharge of the filler, and weight scale readings are measured. This is a measuring means for measuring the time dependency of the load when the viscous liquid is injected from the injection needle by the load applying means.

The shear rate is obtained from weight scale readings, i.e. time derivatives of measurement results by the measuring means. A flow curve, which can be generally evaluated by a rheometer, can be obtained by plotting weight scale readings, i.e. shear stress to this shear rate. That is, a flow curve when a viscous liquid is injected from an injection needle can be obtained from the measurement results by the measuring means. From the obtained flow curve, the fluidity of the viscous liquid can be evaluated.

As the evaluation of fluidity, the thixotropic properties of a gel and the equilibrium constant for the formation of a gel network are obtained from the slope and intercept of double logarithmic plot, the logarithm of shear stress and the logarithm of shear rate. When the slope of double logarithmic plot is near 1, the fluid is Newtonian fluid (a normal liquid in which resistance increases depending on applied force), and when the slope is less than 1, thixotropic properties (properties of behaving as a solid when not applying force, but behaving like a fluid when applying force) are shown, and when the slope is greater than 1, dilatant properties (properties of behaving like a fluid when not applying force, but increasing rigidity depending on force) are shown.

The filler according to the present embodiment shows thixotropic properties, and is almost solid in a syringe, but is easily discharged from a needle when applying force to a plunger. After subcutaneously injected, the filler is solidified and remains at the site into which the filler is injected, and quickly shows the effect of smoothing wrinkles.

Herein, the present invention can be the following embodiments (A) to (I).

The present embodiment (A) is a method for producing an agent for hypodermic injection,
wherein the agent is
an agent including a hydrogel containing sintered hydroxyapatite particles, and
the production method is
a production method including the deaeration step of removing air contained in the agent.

The present embodiment (B) is
a method for producing a syringe containing an agent for hypodermic injection,
wherein the agent is
an agent including a hydrogel containing sintered hydroxyapatite particles, and
the production method is
a production method including
a deaeration step of removing air contained in the agent, and
a step of filling the agent after the deaeration step in the syringe.

The present embodiment (C) is
the production method according to the present embodiment (A) or (B), wherein the deaeration step is a step in which deaeration is carried out by applying the agent to a centrifuge under reduced pressure.

The present embodiment (D) is
the production method according to any of the embodiments (A) to (C), wherein the hydrogel is a carboxymethylcellulose gel.

The present embodiment (E) is
the production method according to any of the embodiments (A) to (D), wherein the viscosity of the agent is 50 to 15000 mPa·s.

The present embodiment (F) is
the production method according to any of the embodiments (A) to (E), wherein the average particle diameter of the sintered hydroxyapatite particles is 15 μm or less.

The present embodiment (G) is
the production method according to the embodiments (A) to (H), wherein 90% or more of the sintered hydroxyapatite particles have a particle diameter of 15 μm or less.

The present embodiment (H) is
the production method according to any of the embodiments (A) to (G), wherein the sintered hydroxyapatite particle content is 1 to 60% by mass based on the total mass of the agent.

The present embodiment (I) is
the production method according to any of the embodiments (A) to (H), wherein the agent passes through a hollow needle with an internal diameter of 0.20 mm or less.

With respect to general cosmetic fillers etc., when a product thereof is directly used, problems in the safety aspect still remain in some cases, for example inflammation can occur. However, according to the above embodiment (A) to (I), it is possible to provide an agent for hypodermic injection and a syringe containing an agent for hypodermic injection that are unlikely to cause inflammation.

EXAMPLES

Example A

<<Production of Agent for Hypodermic Injection>>
<Materials>
CMC-Na
Glycerin
Sintered hydroxyapatite aggregates
Sterile water
<Steps>
Instruments used were sterilized.

Next, 50 g of glycerin was stirred at 300 rpm by a motor-driven propeller shaft. With stirring for above 2 minutes, 5 g of CMC-Na was blended in glycerin and the obtained mixture was stirred for 15 minutes to obtain a solution.

The obtained solution was stirred for above 10 minutes, and the obtained CMC-Na paste was cut into a 1.5 cm square, which was blended in 204 ml of sterile water. This sterile water was stirred for 120 minutes to obtain a CMC-Na hydrogel (viscosity 208 mPa·s).

To 28.0 g of the obtained CMC-Na hydrogel, 12.0 g of sintered hydroxyapatite aggregates were blended in 3 batches and the obtained mixture was stirred for 10 minutes to obtain a crude filler.

Using a propeller, 30.0 g of the obtained crude filler was stirred to obtain an agent for hypodermic injection (HAp blended rate 30% by mass).

Furthermore, agents for hypodermic injection were prepared in the same manner as above except that sintered hydroxyapatite aggregates used were selected from those with a particle diameter of 40 nm, 200 nm, 3 μm, 7 μm, and 25 μm, and a carboxymethylcellulose gel was selected from those with a viscosity of 67.3 mPa·s, 208 mPa·s, and 514 mPa·s, and the HAp blended rate was changed.

<<Evaluation>>

Next, it was evaluated whether the above agents for hypodermic injection were able to pass through a 30 G needle. More particularly, an agent for hypodermic injection was deaerated and then filled in a syringe. Next, the obtained syringe was pushed and the syringeability for 30 G needle of the agent for hypodermic injection in the injector was confirmed. The evaluations were carried out using ⊚ when the agent for hypodermic injection passes smoothly, ○ when there is a little resistance to push, Δ when the strong force is needed to push, and × when it is impossible to push or it is impossible to produce a filler itself. The results are shown in Table 1.

TABLE 1

| Apatite | | | CMC | | Evaluation HAp blended rate | | | | | | | |
|---|---|---|---|---|---|---|---|---|---|---|---|---|
| | | | | | 5% | 10% | 20% | 30% | 40% | 50% | 60% | 65% |
| Hydroxyapatite 1 | 40 nm | CMC-Na1 | (viscosity 208 mPa·s) | | ⊚ | ⊚ | ⊚ | ⊚·✖ | ⊚ | Δ·✖ | Δ | X |
| Hydroxyapatite 2 | 200 nm | CMC-Na1 | (viscosity 208 mPa·s) | | ⊚ | ⊚ | ⊚ | ⊚ | ⊚ | ○ | ○ | X |
| Hydroxyapatite 3 | 3 μm | CMC-Na1 | (viscosity 208 mPa·s) | | ⊚ | ⊚·✖ | ⊚ | ⊚ | ⊚ | ○ | Δ | X |
| Hydroxyapatite 4 | 7 μm | CMC-Na1 | (viscosity 208 mPa·s) | | ⊚ | ⊚ | ⊚ | ⊚·✖ | ⊚·✖ | ⊚ | ○ | X |
| Hydroxyapatite 5 | 25 μm | CMC-Na1 | (viscosity 208 mPa·s) | | X | X | X | X | X | X | X | X |
| Hydroxyapatite 1 | 40 nm | CMC-Na2 (Low viscosity) | (viscosity 67.3 mPa·s) | | ⊚ | ⊚ | ⊚ | ⊚ | ⊚ | ○ | Δ | X |
| Hydroxyapatite 1 | 40 nm | CMC-Na3 (High viscosity) | (viscosity 514 mPa·s) | | ⊚ | ⊚ | ○ | Δ | Δ | Δ | Δ | X |

The samples indicated by ✖ in Table above were further evaluated, and it was verified that the samples evaluated as ⊚ could pass through an injection needle with an internal diameter of 0.12 mm.

The thixotropic index of an agent for hypodermic injection according to each Example was measured by the method described above, and was verified to be 0.1 to 0.3. That is, it is found that the agent for hypodermic injections according to Examples can pass through thin needles and retain under the skin for a sufficient time. It should be noted that, when considering the properties of remaining under the skin, a case having a gel viscosity of 208 mPa·s was better than a case having a gel viscosity of 67.3 mPa·s.

Furthermore, the particle diameters of 100 sintered hydroxyapatite particles (particles in an image taken by a microscope) contained in an agent for hypodermic injection according to each Example were measured, and it was verified that all the particles had a particle diameter of 15 μm or less.

Besides, it was verified that, particularly, in particles with a particle diameter of less than 100 nm, apatite with a smaller particle diameter had a strong tendency to have higher thixotropic properties, i.e. a lower thixotropic index, even in a small amount.

Figure 1A:
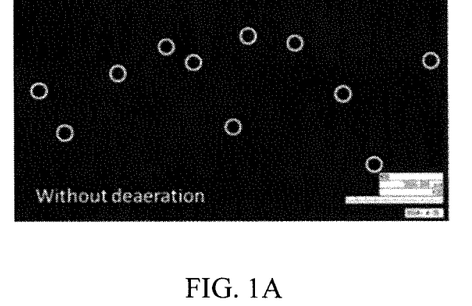
FIG. 1A and FIG. 1B are figures (photographs) showing the filler according to Example before and after the deaeration step.
Figure 1B:
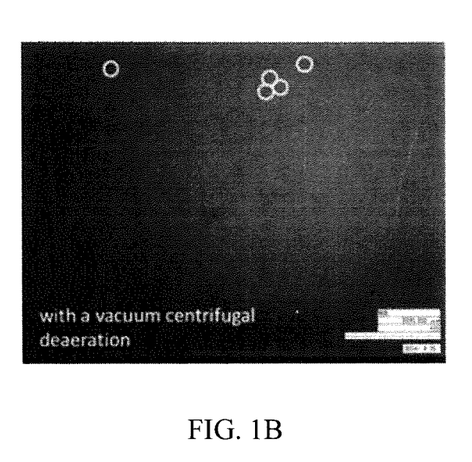

Herein, when the above agent for hypodermic injection was subjected to centrifugal deaeration at (pressure, revolution/rotation ratio, time)=(1.3 KPa, 9/3, 90 sec), deaeration in the agent for hypodermic injection was confirmed. In the evaluation of syringeability for 30 G needle, deaeration properties were higher in the order of ⊚, ○, Δ and ×. FIG.

1A and FIG. 1B are photographs before and after the deaeration step in the case of hydroxyapatite 1, CMC-Na 1 and the HAp blended rate 30% [(a) before deaeration and (b) after deaeration], and the ranges surrounded by circles indicate remaining air.

Example B

<<Production of Agent for Hypodermic Injection>>
<Materials>
CMC-Na
Glycerin
Sintered hydroxyapatite aggregates
Sterile water
<Steps>
Instruments used were sterilized.

Next, 50 g of glycerin was stirred at 300 rpm by a motor-driven propeller shaft. With stirring for above 2 minutes, 5 g of CMC-Na was blended in glycerin and the obtained mixture was stirred for 15 minutes to obtain a solution.

The obtained solution was stirred for above 10 minutes, and the obtained CMC-Na paste was cut into a 1.5 cm square, which was blended in 204 ml of sterile water. This sterile water was stirred for 120 minutes to obtain a CMC-Na hydrogel (viscosity 208 mPa·s).

To 28.0 g of the obtained CMC-Na hydrogel, 12.0 g of sintered hydroxyapatite aggregate was blended in 3 batches and the obtained mixture was stirred for 10 minutes to obtain a crude filler.

Using a propeller, 30.0 g of the obtained crude filler was stirred to obtain an agent for hypodermic injection (HAp blended rate 30% by mass).

Herein, with respect to sintered hydroxyapatite aggregates used, those with a particle diameter of 40 nm, 200 nm, 3 μm, 7 μm and 25 μm were crushed and mixed to prepare sintered hydroxyapatite aggregates in agents for hypodermic injection according to each of Example B1, Example B2, Reference Example B1 and Reference Example B2.

<<Evaluation>>
<Particle Size Distribution>

With respect to agents for hypodermic injection prepared by the above steps, the particle size distribution of apatite particles in each of the agents for hypodermic injection was measured using a Nano Particle Size Analyzer, SALD-7500nano (SHIMADZU CORPORATION). Each of the agents for hypodermic injection is put between slide glasses drawn as much as possible, and the particle size distribution was measured with a refractive index of 1.65. The results are shown in FIG. 1A and FIG. 1B.

<Reaggregation Properties at Heat Sterilization>

Next, agents for hypodermic injection were sterilized with heat at 120° C. and reaggregation properties were observed. The evaluations were carried out using Δ when reaggregation was observed, and ○ when reaggregation was not observed. The results are shown in Table 2.

<Syringeability for 30 G Needle>

Furthermore, it was evaluated whether the above agent for hypodermic injections in which reaggregation did not occur (that is, the agent for hypodermic injections evaluated as ○ in the reaggregation properties at heat sterilization) could pass through a 30 G needle. More particularly, an agent for hypodermic injection was deaerated and then filled in an injector. Next, the obtained injector was pushed and the syringeability for 30 G needle of the agent for hypodermic injection in the injector was confirmed. The evaluations were carried out using ⊚ when the agent for hypodermic injection passes smoothly, ○ when there is a little resistance to push, Δ when the strong force is needed to push, and × when it is impossible to push. The results are shown in Table 2.

TABLE 2

|  | Example B1 | Example B2 | Reference Example B1 | Reference Example B2 |
|---|---|---|---|---|
| Reaggregation properties | ○ | ○ | Δ | Δ |
| Syringeability for 30 G Needle | ⊚ | ⊚ | — | — |

Figure 2:
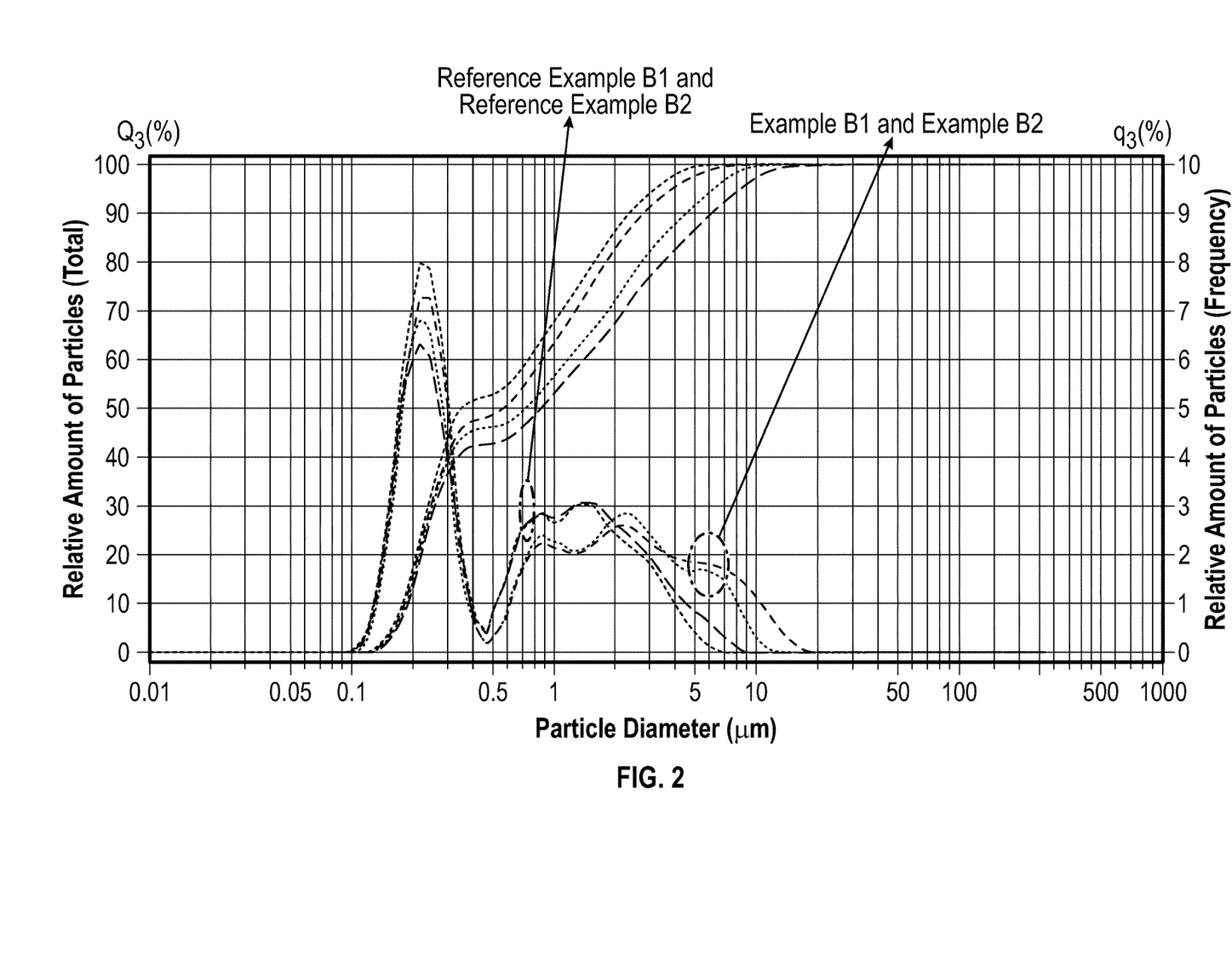
FIG. 2 is a graph showing the results obtained by measuring the particle size distribution of the filler according to Example.

As shown in FIG. 2 and Table 2, reaggregation does not occur in the case of the agent for hypodermic injection according to Example B (4% or more of sintered hydroxyapatite particles have a particle diameter of 5 μm or more and 30 μm or less.)

Furthermore, it was verified that the agents for hypodermic injection according to Example B1 and Example B2, in which reaggregation did not occur, could pass through an injection needle with an internal diameter of 0.12 mm.

The thixotropic index of an agent for hypodermic injection according to each Example was measured by the method described above and verified to be 0.1 to 0.3. That is, it is found that the agent for hypodermic injections according to Examples can pass through a thin needle and furthermore remain under the skin for a significant time.

The invention claimed is:
1. An agent for hypodermic injection comprising:
   a hydrogel containing carboxymethylcellulose and sintered hydroxyapatite particles, wherein
   a content of the sintered hydroxyapatite particles is 1 to 60% by mass based on the total mass of the agent,
   an average particle diameter of the sintered hydroxyapatite particles is 1 μm or less,
   4% or more of the sintered hydroxyapatite particles have a particle diameter that ranges from 5 μm or more to 30 μm or less, and
   a viscosity of the hydrogel is in a range from 60 to 1000 mPa·s.
2. The agent according to claim 1, wherein 90% or more of the sintered hydroxyapatite particles have a particle diameter of 1 μm or less.
3. The agent according to claim 1, wherein the sintered hydroxyapatite particles are for promoting collagen production.
4. The agent according to claim 1, wherein the agent passes through a hollow needle with an internal diameter of 0.20 mm or less.
5. A method for producing an agent for hypodermic injection, the method comprising:
   a step of mixing sintered hydroxyapatite particles and a carboxymethylcellulose hydrogel, wherein
   a content of the sintered hydroxyapatite particles is 1 to 60% by mass based on the total mass of the agent,
   an average particle diameter of sintered hydroxyapatite particles in the agent is 1 μm or less,
   4% or more of the sintered hydroxyapatite particles have a particle diameter that ranges from 5 μm or more to 30 μm or less, and
   a viscosity of the hydrogel is in a range from 60 to 1000 mPa·s.

6. The production method according to claim 5, wherein 90% or more of sintered hydroxyapatite particles in the agent have a particle diameter of 1 µm or less.

7. The production method according to claim 5, wherein the sintered hydroxyapatite particles are for promoting collagen production.

8. The production method according to claim 5, wherein the agent passes through a hollow needle with an internal diameter of 0.20 mm or less.

9. The agent according to claim 1, wherein a half width of the peak of the (300) plane around $2\theta=32°$ in X-ray diffraction (CuK α line) of the sintered hydroxyapatite particles is 0.8 or less.

10. The production method according to claim 5, wherein a half width of the peak of the (300) plane around $2\theta=32°$ in X-ray diffraction (CuK α line) of the sintered hydroxyapatite particles is 0.8 or less.

* * * * *